(12) United States Patent
Wallace et al.

(10) Patent No.: US 6,292,689 B1
(45) Date of Patent: Sep. 18, 2001

(54) APPARATUS AND METHODS OF BIOELECTRICAL IMPEDANCE ANALYSIS OF BLOOD FLOW

(75) Inventors: Arthur W. Wallace, San Rafael, CA (US); Ascher Shmulewitz, Tel Aviv (IL)

(73) Assignee: Imagyn Medical Technologies California, Inc., Irvine, CA (US)

( * ) Notice: Subject to any disclaimer, the term of this patent is extended or adjusted under 35 U.S.C. 154(b) by 0 days.

(21) Appl. No.: 09/458,186

(22) Filed: Dec. 8, 1999

Related U.S. Application Data

(63) Continuation-in-part of application No. 08/934,036, filed on Sep. 19, 1997, now Pat. No. 6,095,987, and a continuation of application No. PCT/US97/06369, filed on Apr. 17, 1997, which is a continuation-in-part of application No. 08/726,822, filed on Oct. 4, 1996, now Pat. No. 5,782,774, which is a continuation-in-part of application No. 08/634,758, filed on Apr. 17, 1996, now Pat. No. 5,791,349.

(51) Int. Cl.⁷ .................................................. A61B 5/05
(52) U.S. Cl. ........................................ 600/547; 600/587
(58) Field of Search .................................. 600/547, 587, 600/595

(56) References Cited

U.S. PATENT DOCUMENTS

| | | |
|---|---|---|
| 3,340,867 | 9/1967 | Kubicek et al. . |
| 3,651,318 | 3/1972 | Czekajewski . |
| 3,726,269 | 4/1973 | Webster, Jr. . |
| 3,915,155 | 10/1975 | Jacobson et al. . |
| 4,437,469 | 3/1984 | Djordjevich et al. . |
| 4,450,527 | 5/1984 | Sramek . |
| 4,671,295 | 6/1987 | Abrams et al. . |
| 4,722,347 | 2/1988 | Abrams et al. . |
| 4,836,214 | 6/1989 | Sramek . |
| 4,852,580 | 8/1989 | Wood . |
| 4,870,578 | 9/1989 | Vysin et al. . |
| 4,953,556 | 9/1990 | Evans . |
| 4,967,759 | 11/1990 | Teves . |
| 5,005,573 | 4/1991 | Buchanan . |
| 5,024,228 | 6/1991 | Goldstone et al. . |
| 5,080,107 | 1/1992 | Teves . |
| 5,125,406 | 6/1992 | Goldstone et al. . |
| 5,203,344 | 4/1993 | Scheltinga et al. . |
| 5,379,765 | 1/1995 | Kajiwara et al. . |
| 5,453,086 | 9/1995 | Weber . |
| 5,469,859 | 11/1995 | Tsoglin et al. . |
| 5,477,860 | 12/1995 | Essen-Moller . |

OTHER PUBLICATIONS

"Bioelectrical Impedanc Analysis in Body Composition Measurement", *National Institute of Health Technology Assessment Conference Statement*, Dec. 12–14, 1994, pp. 3–35.

(List continued on next page.)

*Primary Examiner*—Eric F. Winakur
*Assistant Examiner*—Pamela L. Wingood
(74) *Attorney, Agent, or Firm*—Fish & Neave; Nicola A. Pisano

(57) ABSTRACT

Apparatus and methods are provided for monitoring cardiac output using bioelectrical impedance techniques in which three orthogonal pairs of sense electrodes are placed in the trachea or esophagus in the vicinity of the aorta, while an excitation current is injected into the intervening tissue mass via a current electrode, so that bioelectrical impedance measurements based on the voltage drop sensed by the sense electrodes reflect voltage changes induced primarily by blood flow dynamics. Methods are provided for computing cardiac output from bioelectrical impedance values using a multi-parameter algorithm derived using stepwise multiple linear regression or other optimization techniques. Apparatus and methods are also provided so that the measured cardiac output may be used to control administration of intravenous fluids or medication to an organism or to optimize a heart rate controlled by a pacemaker.

43 Claims, 6 Drawing Sheets

OTHER PUBLICATIONS

"Continuous Cardiac Output Monitoring by Electrical Bio-impedance", *American College of Cardiology*, Jun. 1988, pp. 1–7.

B. Bhattacharya et al., "Potential Distribution in the Thorax in Relation to Electrical Field Plethysmography", *Medical & Biological Engineering & Computing*, May 1988, pp. 303–309.

F.H. Bonjer, M.D., et al., "The Origin of the Variations of Body Impedance Occurring During the Cardiac Cycle", *Circulation*, vol. VI, Sep. 1952, pp. 415–420.

David E. Clarke, M.D., et al., "Thoracic Electrical Bio-impedance Measurement of Cardiac Output—Not Ready for Prime Time", *Critical Care Medicine*, vol. 21, No. 8, Aug. 1993, pp. 1111–1112.

H. Fuller, et al., "The Current Status and Future Directions of Impedance Cardiography in ICU", *Annals of Biomedical Engineering*, vol. 17, 1989, pp. 483–493.

David B. Geselowitz, "An Application of Electrocardiographic Lead Theory to Impedance Plethysomography", *IEEE Transactions on Bio–Medical Engineering*, vol. BME–18, No. 1, Jan. 1971, pp. 38–41.

Joseph C. Greenfield, Jr., M.D., et al., "Relation Between Pressure and Diameter in the Ascending Aorta of Man", *Circulation Research*, vol. X, May 1962, pp. 778–781.

Harry Handelsman, D.O., "Public Health Service Assessment Cardiac Output by Electrical Bioimpedance", *Health Technology Assessment Reports: Cardiac Output by Electrical Bioimpedance*, No. 3, 1989, pp. 1–5.

Deok W. Kim et al, "Origins of the Impedance Change in Impedance Cardiography by a Three–Dimensional Finite Element Model", *IEEE*, 1988, pp. 993–1000.

W.G. Kubicek, "On the source of Peak First Time Derivative (dZ/dt) During Impedance Cardiography", *Annals of Biomedical Engineering*, vol. 17, 1989, pp. 459–462.

John Lehr, "A Vector Derivation Useful in Impedance Plethysmographic Field Calculations", *IEEE Transactions on Biomedical Engineering*, Mar. 1972, pp. 156–157.

Henry C. Lukaski, PhD, et al., "Estimation of body Fluid Volumes Using Tetrapolar Bioelectrical Impedance Measurements", *Aviation, Space and Environmental Medicine*, Dec. 1988, pp. 1163–1169.

Daniel S. Miles, PhD et al., "Impedance Cardiography: Noninvasive Assessment of Human central Hemodynamics at Rest and During Exercise", *Exercise and Sport Sciences Reviews*, vol. 17, 1989, pp. 231–263.

Christos G. Pappas, M.D. et al., "Impedance Cardiography in the Measurement of Cardiac Output: Studies in Rabbits", *Journal of Surgical Research*, 59, 1995, pp. 504–510.

R.P. Patterson, "Fundamentals of Impedance Cardiography", *IEEE Engineering in Medicine and Biology Magazine*, Mar. 1989, pp. 35–38.

Bill C. Penney, PhD., et al., "An Overview of the Theory and Some Applications of Impedance Plethysmography", *IEEE Frontiers of Engineering in Health Care*, 1981, pp. 169–173.

Andrew Sherwood et al., "Committee Report; Methodological Guidelines for Impedance Cardiography", *Psychophysiology*, Feb. 1989, pp. 1–38.

William C. Shoemaker, MD, FCCM, et al., "Multicenter Trial of a New Thoracic Electrical Bioimpedance Device for Cardiac Output Estimation", *Critical Care Medicine*, vol. 22, No. 12, 1994, pp. 1907–1912.

Joseph M. VanDeWater, M.D. et al., "Development and Evaluation of a New Impedance Cardiograph", *Journal of Clinical Engineering*, May/Jun. 1995, pp. 218–223.

Li Wang, "Contributions of Heart Movement and Blood Volume Change to Impedance Cardiography Calculated by Human Thorax Models", *IEEE*, 1993, pp. 808–809.

Li Wang, "Multiple Sources of the Impedance Cardiogram Based on 3–D Finite Difference Human Thorax Models", *IEEE*, 1995, pp. 141–148.

Klaas R. Visser, Electrical Properties of Flowing Blood and Impedance Cardiography, *Annals of Biomedical Engineering*, vol. 17, 1989, pp. 463–473.

Xiang Wang, PhD et al., "Time–Frequency Distribution Technique in Biological Signal Processing", *Biomedical Instrumentation & Technology*, May–Jun. 1995, pp. 203–212.

APPARATUS AND METHODS OF BIOELECTRICAL IMPEDANCE ANALYSIS OF BLOOD FLOW

REFERENCE TO RELATED APPLICATIONS

This application is a continuation of is a continuation-in-part of U.S. patent application Ser. No. 08/934,036, filed Sep. 19, 1997, now U.S. Pat. No. 6,095,987, entitled "APPARATUS AND METHODS OF BIOELECTRICAL IMPEDANCE ANALYSIS OF BLOODFLOW," which PCT/US97/06369, filed Apr. 17, 1997, which is a continuation-in-part of U.S. patent application Ser. No. 08/726,822, now U.S. Pat. No. 5,782,774, filed Oct. 4, 1996, entitled "APPARATUS AND METHODS OF BIOELECTRICAL IMPEDANCE ANALYSIS OF BLOOD FLOW," which is a continuation-in-part of U.S. patent application Ser. No. 08/634,758, now U.S. Pat. No. 5,791,349 filed Apr. 17, 1996, entitled "APPARATUS AND METHODS OF BIOELECTRICAL IMPEDANCE ANALYSIS OF BLOOD FLOW."

FIELD OF THE INVENTION

The present invention relates generally to apparatus and methods for non-invasively measuring cardiac output and, more particularly, to apparatus and methods for measuring cardiac output using bioelectrical impedance analysis techniques.

BACKGROUND OF THE INVENTION

Knowledge of cardiac output is crucial in the care of critically ill patients, as well as patients with chronic heart disease requiring monitoring of medication. For many years the standard of cardiac output measurement has been pulmonary artery catheterization. Previously known catheterization techniques, as described, for example, in U.S. Pat. Nos. 3,915,155, 3,726,269 and 3,651,318, involve periodic injection into the patient's bloodstream of a bolus of saline, during which thermodilution measurements are performed to determine cardiac output. Such techniques cannot generally be used for continuous monitoring. Moreover, such catheterization techniques pose significant risk to the patient, including malignant arrhythmias, pulmonary artery rupture, and in rare cases, death.

Consequently, for many years work has been underway to develop less invasive apparatus and methods for monitoring cardiac output. For example, as an alternative to catheterization methods, Doppler ultrasound techniques have been adapted to measure the velocity of blood flow. If the diameter of a vessel, its flow profile, and the angle of the ultrasound beam relative to the vessel can be determined, Doppler ultrasound measurements of the ascending aorta, either externally (from the suprasternal notch) or internally (from within the trachea) can be used as a measure of cardiac output.

U.S. Pat. No. 4,671,295 describes an example of such methods and apparatus, wherein an ultrasound transducer is mounted on the tip of an endotracheal tube so that Doppler measurements of blood flow from a point (pulse wave mode) or path (continuous wave mode) along the ultrasound beam can be measured. The method described in the patent requires multiple measurements within the blood vessel, a priori knowledge of the blood flow pattern and cross-sectional area of the vessel, and the relative angulation of the blood vessel. In addition, the measurement is highly dependent upon the exact placement of the transducer. These drawbacks have resulted in the slow adoption of Doppler ultrasound cardiac output techniques.

A yet further technique which the prior art has sought to apply to the measurement of cardiac output is bioelectrical impedance analysis ("BIA"). BIA has recently gained wide use as a method for measuring body composition and physiological metrics. BIA involves passing a low level electrical alternating current ("AC") through body tissues between multiple electrodes, measuring the voltage difference between multiple locations on the tissue, and then calculating the electrical impedance (electrical resistance plus reactance) of the stimulated tissue.

Generally, BIA apparatus employ two current electrodes to conduct a low level excitation current through body tissue. As current flows in the tissue, a potential difference develops across the tissue which is proportional to the value of the AC current and the tissue impedance. The tissue impedance may be calculated by disposing two sense electrodes between the current electrodes and measuring the voltage difference between the two sense electrodes.

Current flows predominantly through body materials with high conductivity, such as blood. Less current flows through muscle, which has an intermediate conductivity, while the conductivity of fat, air and bone is much lower than that of either blood or muscle. Because the resistance to current flow is a function of the conductivity and cross-sectional area of the conducting volume, volumes having a larger cross-sectional area have lower electrical resistance.

It is also known that the impedance of the conducting volume and the measured medium metrics (i.e., static parameters such as fat or water content, and dynamic metrics, such as blood flow) are dependent upon the placement of the electrodes and the conducting path between the electrodes. Thus, the greater the distance between the electrodes, the more likely that extraneous variables will affect the measurement.

Previously known BIA methods generally correlate the measured voltage drop between the sense electrodes to tissue impedance using relatively simple algorithms based on simplified models of body structure, for example, by assuming that the body is composed of simple cylindrical resistive volumes. Temporal cyclical variations in the body impedance are then assumed to result from physiological events such as blood flow and breathing.

Measurements of the electrical impedance, and particularly, the time-varying nature of electrical impedance, may therefore provide a non-invasive indicator of physiological events. Various algorithms have been developed to isolate specific physiological parameters, such as cardiac output, from the measured bioelectrical impedance, as described, for example, in W. G. Kubicek, et al., "Development And Evaluation Of An Impedance Cardiac Output System," Aerospace Medicine, Vol. 37, pp. 1208–1212 (1966) and U.S. Pat. No. 3,340,862, which is incorporated herein by reference.

Despite the application of BIA methods for measuring cardiac output, no simple continuous BIA-based cardiac output measurement device has gained widespread acceptance. Many existing BIA devices use external or internal electrodes to measure bioelectrical impedance for large volumes, for example, the whole body or thoracic segments. Because the excitation current diffuses throughout the entire volume, making use of any and all conductive paths, differences between individual patients, and even for the same patient over time, may inhibit standardizing the BIA metrics.

Moreover, it is known that while BIA measurements of cardiac output provide good correlation for normal patients and those hemodynamically stable patients, there is poorer correlation for critically ill patients and patients in heart failure, as described, for example, in R. J. Detemeter et al., "The Use Of Noninvasive Bioelectric Impedance To Determine Cardiac Output: Factors Affecting Its Accuracy," *Am. J. Noninvasive Cardiol.*, Vol. 2, pp. 112–118 (1988).

An example of an attempt to overcome the variabilities encountered when taking bioelectrical impedance measurements across large volumes is described, for example, in U.S. Pat. No. 4,870,578. That patent describes BIA apparatus for monitoring cardiac output by using external electrodes that measure the electrical resistance of a segment of the thorax and includes circuitry to account for respiratory-induced voltage changes. As acknowledged in that patent, the respiratory-induced voltage changes are typically much greater than the cardiac-induced voltage changes.

Other devices that attempt to account for the effect of non-cardiac physiological events on bioelectrical impedance include arranging multiple electrodes on esophageal catheters to measure thoracic bioelectric impedance, as described, for example, in U.S. Pat. Nos. 4,852,580 and 4,836,214. Both patents describe multi-electrode arrays inserted into the esophagus to provide an impedance measurement reflecting blood flow in the descending aorta. It may be difficult for such devices to provide true isolation of cardiac-induced voltage changes from those induced by other physiological events. In addition, these systems do not ensure that the multiple electrodes make positive contact with the esophageal wall.

BIA measurements have also been employed to provide a metric of cardiac output by measuring physiologic effects other than blood flow. For example, U.S. Pat. No. 4,953,556 describes a BIA arrangement including an internal electrode mounted on an esophageal catheter and an external electrode which is disposed above the apex of the heart. The apparatus described in that patent attempts to use BIA measurements to determine cardiac wall motion and lung motion, from which an estimate of cardiac output and pulmonary activity can be obtained.

BIA measurements taken across small volumes, such as just the ascending aorta, are typically highly dependent on the position and orientation of the electrodes that are used to measure the impedance. For example, a pair of electrodes positioned orthogonally to the flow will provide radically different measurements than a pair of electrodes that are placed parallel to the direction of flow. Given the complex curvature of the aorta, it can be very difficult to align and orient a pair of electrodes to provide useful BIA measurements.

In view of the foregoing, it would be desirable to provide apparatus and methods for accurately, non-invasively and continuously measuring cardiac output using BIA techniques.

It further would be desirable to provide apparatus and methods for measuring cardiac output in critically ill patients using BIA techniques that overcome the inaccuracies arising from measuring voltage changes across whole body or large volume thoracic segments.

It also would be desirable to provide apparatus and methods for measuring cardiac output using BIA techniques that are less dependent on the precise positioning and orientation of the electrodes than previously known BIA cardiac output measurement devices and methods.

It also would be desirable to provide inexpensive apparatus and methods for measuring cardiac output using BIA techniques that overcome the drawbacks of previously known BIA cardiac output measurement devices and methods.

It would further be desirable to provide apparatus and methods for continuously monitoring cardiac output so as to permit the measured cardiac output to be employed as a metric for controlling and maintaining other aspects of a patient's health.

SUMMARY OF THE INVENTION

In view of the foregoing, it is an object of this invention to provide apparatus and methods for accurately, non-invasively and continuously measuring cardiac output using BIA techniques.

It is another object of this invention to provide apparatus and methods for measuring cardiac output in critically ill patients using BIA techniques that overcome the inaccuracies arising from measuring voltage changes across the whole body or large volume thoracic segments.

It also is an object of the present invention to provide apparatus and methods for measuring cardiac output using BIA techniques that are less dependent on the precise positioning and orientation of the electrodes than previously known BIA cardiac output measurement devices and methods.

It is yet another object of the present invention to provide inexpensive apparatus and methods for measuring cardiac output using BIA techniques that overcome the drawbacks of previously known BIA cardiac output measurement devices and methods.

It is still another object of this invention to provide apparatus and methods for continuously monitoring cardiac output that permit the measured cardiac output to be employed as a metric for controlling and maintaining other aspects of a patient's health.

These and other objects of the invention are accomplished in accordance with the principles of the invention by providing BIA cardiac output monitoring apparatus adapted to be disposed within a patient's trachea or esophagus in close relation to the aorta to acquire cardiac output information. Preferred embodiments of the apparatus of the present invention include: 1) multiple sense electrodes configured to be placed in the patient's trachea or esophagus in the vicinity of the aorta, wherein the sense electrodes are arranged in pairs along three orthogonal axes; and 2) a current electrode and a ground electrode disposed within the patient's trachea or esophagus.

In accordance with the principles of the invention, current conducted between the current electrode and the ground electrode flows throughout the intervening thoracic mass, and passes preferentially through blood because of its high conductivity, relative to other body materials. The sense electrodes primarily sense the voltage drop in the blood in the aorta. Because the impedance of the blood in the aorta changes with the volume of blood flowing through the aorta, the measured voltage drop between the sense electrodes varies with blood flow. Time-varying differences in the sensed voltage, therefore, primarily are caused by blood flow dynamics, rather than respiratory or non-cardiac related physiological effects.

Measuring the impedance along three orthogonal axes enables a three-dimensional impedance field to be computed, which in turn is used to compute a stroke volume. Use of three-dimensional BIA measurements and algorithms provides a degree of invariance to the precise positioning and orientation of the sense electrodes.

Methods in accordance with the present invention overcome the inaccuracies of the gross physiologic models employed in previously known BIA cardiac methods, by avoiding the simplified algorithms for the ventricular stroke volume based on whole thorax BIA measurements. In particular, the methods of the present invention employ multiple linear regression or other optimization techniques such as adaptive filtering or neural networks to derive a multi-parameter algorithm that relates impedance measurements made in the vicinity of the aorta along three orthogonal axes to ventricular stroke volume. This multi-parameter algorithm provides an accurate metric for stroke volume that is substantially invariant to the position and orientation of the sense electrodes.

In further aspects of the present invention, apparatus for monitoring a patient's cardiac output may be used to control administration of intravenous fluids and medication to a patient or to optimize heart rate for those patients having pacemakers.

BRIEF DESCRIPTION OF THE DRAWINGS

Further features of the invention, its nature and various advantages will be more apparent from the accompanying drawings and the following detailed description of the preferred embodiments.

DETAILED DESCRIPTION OF THE INVENTION

Figure 1A:
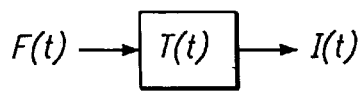
FIGS. 1A and 1B are idealized models of the volumes upon which previously known bioelectrical impedance algorithms are based.

The present invention relates generally to BIA apparatus for use in measuring cardiac output in patients, including critically ill and heart-diseased patients, as well as patients undergoing elective surgery. The apparatus and methods of the present invention overcome drawbacks observed in previously known attempts to use whole body or large volume thoracic BIA measurements to measure cardiac output, by providing apparatus and methods that are not based upon the gross modeling of physiological events implicit in such previously known BIA measurement techniques. Additionally, the BIA measurement apparatus and methods of the present invention are easier to use and provide greater invariance to placement and orientation of electrodes than previously known BIA measurement apparatus and techniques.

In a first embodiment of the apparatus and methods of the present invention, three orthogonal pairs of sense electrodes disposed on an endotracheal tube are used to measure a three-dimensional impedance field. The electrodes are placed in contact with a patient's airway (e.g., trachea and/or bronchus) in close relation to the aorta, so that changes in bioelectrical impedance can be closely correlated to cardiac events, without significant effects due to non-cardiac physiologic events. Excitation AC current is injected into the body between a current electrode and a ground electrode disposed along the endotracheal tube. A second embodiment uses a similar arrangement of electrodes disposed along an esophageal tube or esophageal stethoscope.

In both embodiments, a three-dimensional bioelectrical impedance field is computed from the voltage drop measured between the pairs of sense electrodes. The bioelectrical impedance is in turn correlated to blood flow through the ascending aorta. Because the ascending aorta has no other branches other than the coronary arteries, blood flow through the ascending aorta may be closely correlated to cardiac output.

It is known in the medical literature that BIA measurements of cardiac output in general show good correlation for normal patients and hemodynamically stable patients, but much poorer correlation for critically ill patients, and patients in heart failure, as discussed in the above-mentioned Detemeter paper. It has been discovered that the reason for this poorer correlation in the latter cases is that the theoretical basis underlying the use of whole body or large volume thoracic measurements may be incorrect.

While the present invention finds ready application in monitoring cardiac output in critically-ill and heart diseased patients, it may be advantageously used for all intubated patients, including pediatric cases. For example, apparatus constructed in accordance with the present invention may be readily employed in asymptomatic patients undergoing elective surgery. As many as 95% of post-operative deaths in the latter population result from hemodynamic failure.

Previously known techniques derive the equation for ventricular stroke volume ("SV") from the assumption that a time-varying column of blood, in parallel with the other conducting material in the thorax, changes from zero to the full stroke volume during the cardiac cycle. The column of blood is assumed to be the length between the electrodes used to obtain the BIA measurements, with effects on the BIA measurements due to respiration accounted for, for example, as discussed in the aforementioned U.S. Pat. No. 4,870,578.

FIG. 1A illustrates a typical previously known BIA algorithm. Cardiac output is estimated from the bioelectrical impedance measurement I(t), where it is assumed that changes in the bioelectrical impedance coincidental with the heart electrical activity (as represented by an electrocardiograph output) are the result of blood flow F(t). A transfer function T(t) is then based upon empirical formulae derived from measurements taken on healthy, hemodynamically stable subjects. The bioelectrical impedance I(t) is then computed as:

$$I(t)=F(T)*T(t) \quad (1)$$

It has been determined, however, that the foregoing assumption regarding the column of blood ignores the branched, multiple and complex paths present in the arterial system. Moreover, the distribution of blood and fluids between different physiologic "compartments" in the idealized thoracic or whole body model and body regions are different in normal and critically ill patients.

Figure 1B:
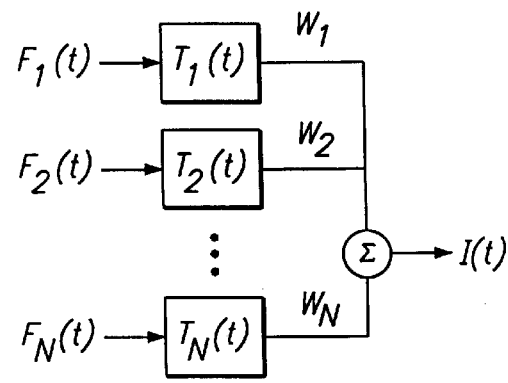

FIG. 1B illustrates that the thoracic approach to BIA measurement must account for transfer functions appropriate to each of the multiple blood flow paths through the volume, so that bioelectrical impedance I(t) should be computed as:

$$I(t) = \Sigma F_i(t) * T_i(t) * W_i \tag{2}$$

where $W_i$ are weights corresponding to a priori knowledge of the relative distribution of flow through the various segments of the volume, e.g., the aorta, and arterial segments and other fluid chambers. Moreover, the weights $W_i$ may be different for different patients, may be different for chronically ill as opposed to healthy subjects, and may be variable even within a given patient, e.g., due to changes in heart rate.

It has been discovered, however, that equation (1) may be used accurately for any patient provided that the transfer function T(t) is correlated to measured blood flow (e.g., using a flow meter) so that the effect of the distribution weights $W_i$ can be essentially eliminated. Accordingly, applicant has concluded that BIA measurements should be taken very close to a major blood vessel or artery, so that between the electrodes of the BIA apparatus there are few or no branching vessels or adjacent vessels. The present invention therefore involves the use of BIA measurements in the vicinity of blood vessels meeting the foregoing requirements, especially the ascending aorta.

Figure 2A:
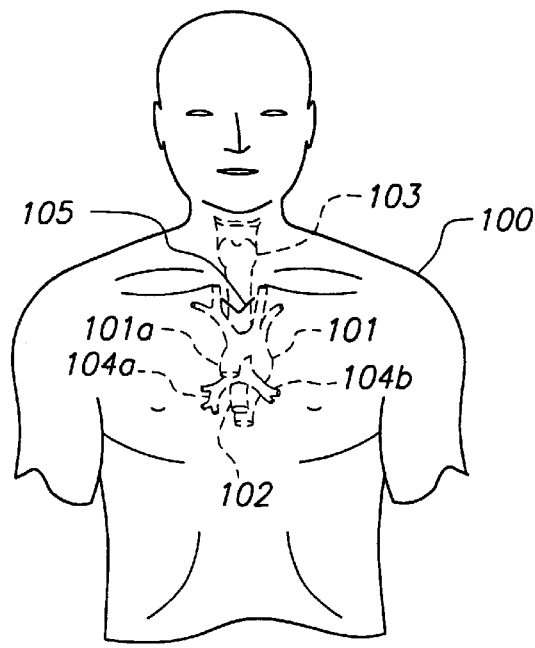
FIGS. 2A and 2B are a vertical frontal view of the upper portion of a human body and a front view of the ascending aorta, the esophagus and the trachea, respectively.
Figure 2B:
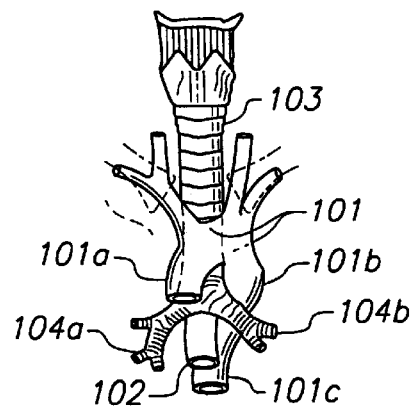

Referring to FIG. 2A, the upper portion of a human body 100 is shown in outline with the corresponding locations of aorta 101, esophagus 102, trachea 103, and bronchi 104a and 104b (all shown in dotted line) and suprasternal notch 105. These internal vessels and organs are more clearly depicted in FIG. 2B. With reference to FIGS. 2A and 2B, the outflow tract of the left ventricle of the heart is ascending aorta 101a. Segment 101b of the artery (the aortic arch) passes in front of right bronchus 104a, in front of trachea 103 and then arches behind left bronchus 104b into the descending aorta 101c, which leads towards the lower part of the body.

Since ascending aorta 101a passes in close proximity to bronchi 104a and 104b and trachea 103, it is possible to obtain a BIA measurement across ascending aorta 101a, with relatively little intervening tissue, by positioning sense electrodes at this location. AC voltage applied to the patient's tissue by current electrodes, positioned in proximity to the patient's ascending aorta, causes an AC current to flow in the patient's tissue. The measured voltage difference between the sense electrodes is then employed to compute tissue impedance. Because the first branches from the aorta (other than the coronary arteries) are from aortic arch 101b, downstream of the measurement location, the measurement of blood flow from ascending aorta 101a accurately measures the volume of blood ejected from the left ventricle.

In previously-known BIA measurement systems, the orientation of electrodes on or near the aorta are expected to have a large effect on both the magnitude and the type of signal produced by the sense electrodes. For example, experiments using a rigid plastic pipe have shown that electrodes placed orthogonal to flow generate a signal that varies linearly with flow in the pipe, while electrodes placed parallel to flow detect changes in flow and the presence or absence of turbulence. As will of course be appreciated, the intra-thoracic aorta is not a straight rigid pipe. As can be seen in FIGS. 2A and 2B, the aorta in the region of interest makes a complex (i.e. more than 180 degree) turn. Since the orientation of the electrodes with respect to flow is important, and it is difficult to identify the exact orientation of an electrode with respect to the aorta, previously-known BIA methods are believed not to produce reliable or reproducible results.

In accordance with the principles of the present invention, the impact of electrode orientation on BIA measurement apparatus and methods is reduced by measuring a three-dimensional impedance field, and using algorithms that relate the three-dimensional impedance field to cardiac output. Measurement of the three-dimensional impedance field is accomplished using three orthogonal pairs of sense electrodes positioned near the aorta, as discussed in detail hereinbelow.

It will be understood by one skilled in the art that as used herein, the three orthogonal pairs of sense electrodes are substantially orthogonal, but need not be precisely orthogonal in a mathematical sense. Considerable variation from a precise orthogonal relationship between the pairs of the electrodes is acceptable, and will provide clinically useful results.

Figure 3:
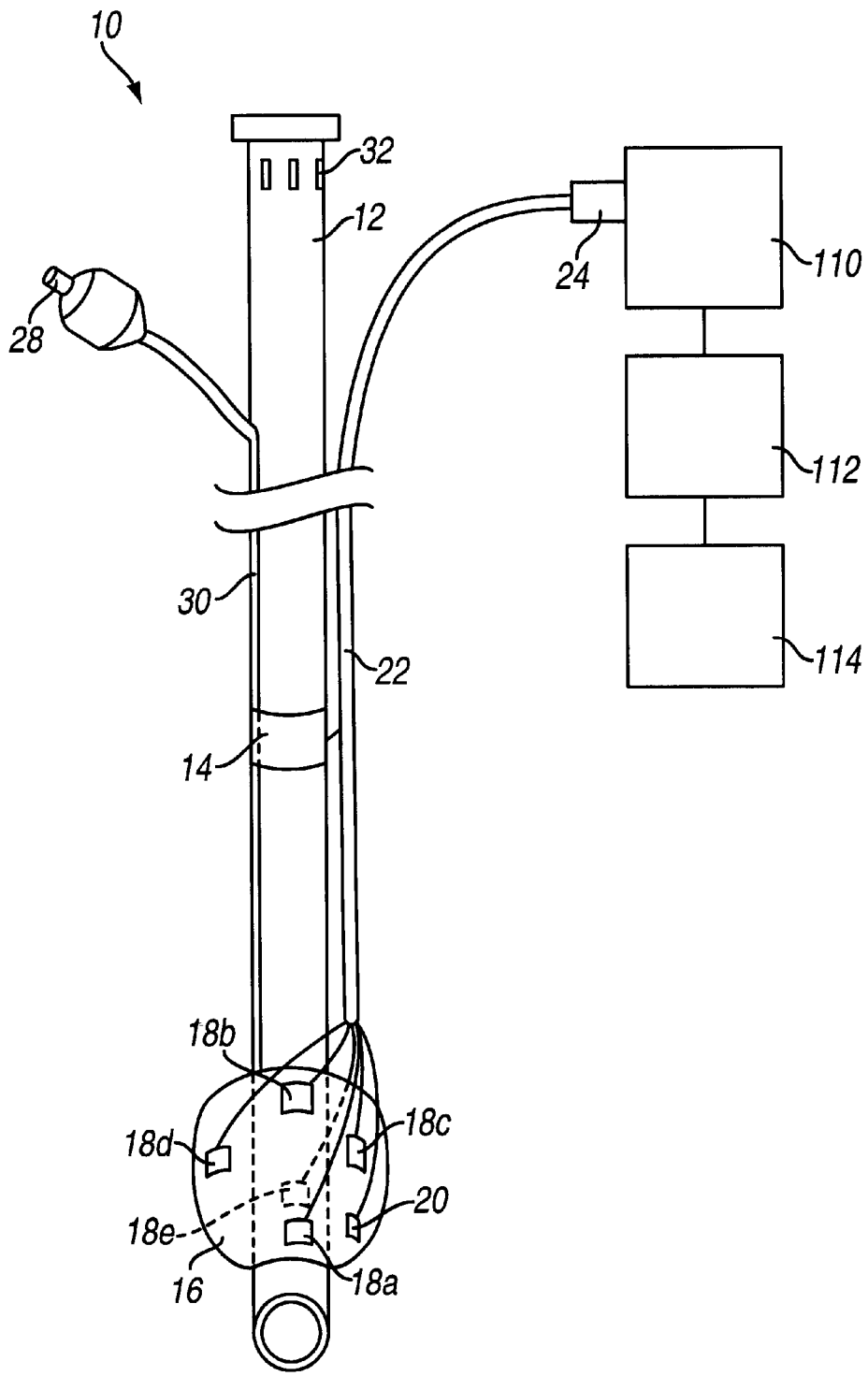
FIG. 3 shows a first embodiment of the apparatus of the present invention for endotracheal use, including three orthogonal pairs of sense electrodes for making a three-dimensional impedance measurement.

Referring now to FIG. 3, a first embodiment of a BIA measurement device built in accordance with the principles of the present invention is described. Measurement apparatus 10 includes endotracheal tube 12, including inflatable cuff 16 disposed near a distal end of endotracheal tube 12, and a lumen for ventilating the patient. Additionally, endotracheal tube 12 includes shaft electrode 14, which serves as an electrical ground electrode for measurement apparatus 10. Sense electrodes 18a–18e are mounted on inflatable cuff 16 to form three orthogonal pairs of sense electrodes. Additionally, current electrode 20 is mounted on inflatable cuff 16.

All of the electrodes, including shaft electrode 14, sense electrodes 18a–18e, and current electrode 20 are connected via cable 22 and connector 24 to impedance recorder 110. Cable 22 may comprise a shielded cable containing multiple conductors or a ribbon cable, and may be disposed within endotracheal tube 12, parallel to endotracheal tube 12, or wrapped around endotracheal tube 12. Measurement apparatus 10 also includes digital sampler 112, and computer 114.

Sense electrodes 18a–18e, current electrode 20, and shaft electrode 14 are preferably composed of a conductive silver ink, printed or silk screened onto a polyethylene backing. Sense electrodes 18a–18e and current electrode 20 are preferably each 6 mm square, while shaft electrode 14 preferably comprises a 15 mm wide band disposed on the shaft of endotracheal tube 12. All of the electrodes have a smooth surface, and are atraumatic to the tracheal mucosa.

The interior of inflatable cuff 16 is in fluid communication with insufflation port 28 via lumen 30 of endotracheal tube 12. When inflated, inflatable cuff 16 retains endotracheal tube 12 in position within the patient's airway, and provides a substantially airtight seal, thereby preventing inadvertent movement of the endotracheal tube. Inflatable cuff 16 also urges sense electrodes 18a–18e and current electrode 20 into contact with the interior wall of the trachea. Inflatable cuff 16 may be inflated using conventional inflation means (i.e., a gas filled syringe) connected to insufflation port 28 via lumen 30. Alternatively, inflatable cuff 16 may be replaced by another suitable type of expandable member for urging the sense electrodes against the interior wall of the patient's airway, such as an expanding mandrel, or other mechanical arrangement.

The proximal end of endotracheal tube 12, i.e., the end manipulated by the clinician, may include reference marks 32 on the circumference of the tube that reflect the circumferential orientation of endotracheal tube 12 within the patient's trachea. The reference marks may be used to assist in placement of the sense electrodes and current electrode. Endotracheal tube 12 may also include a depth marker (not shown) to assist in determining the proper depth of placement.

In use, endotracheal tube 12 is inserted into the patient through the oral or nasal cavity, past the epiglottis and into the trachea in accordance with standard intubation practice. Alternatively, access to the trachea may be had through a surgical opening at the suprasternal notch by conventional tracheotomy.

Endotracheal tube 12 is positioned so that inflatable cuff 16 is located near the aorta, and inflatable cuff 16 is inflated, causing sense electrodes 18*a*–18*e* and current electrode 20 to contact the tracheal mucosa. Shaft electrode 14 contacts the oral mucosa several centimeters above the aorta, and serves as a ground electrode.

An alternating current, preferably a sinusoidal current having a predetermined frequency, is applied between current electrode 20 and shaft electrode 14 by impedance recorder 110. The alternating current preferably has an amplitude of approximately 2 mA, and a frequency in the range of 5 KHz to 1 MHZ, typically 100 KHz. It should be noted that at frequencies below 1 KHz, cardiac stimulation can occur.

Signals indicative of a drop in voltage between the two electrodes of each of the orthogonal pairs of electrodes are received at impedance recorder 110. The first orthogonal pair of electrodes comprises sense electrodes 18*a* and 18*b*, the second orthogonal pair of electrodes comprises sense electrodes 18*c* and 18*d*, and the third orthogonal pair comprises sense electrodes 18*a* and 18*e*.

These impedance signals are digitally sampled at fixed intervals, preferably approximately 400 samples per second, by digital sampler 112. The digital samples are provided to computer 114, which may record the samples, display graphs of the samples, apply algorithms in accordance with the principles of the present invention to determine cardiac output, and apply any additional algorithms to the digital samples.

Impedance recorder 110, digital sampler, and computer 112 may also record and digitize electrocardiogram (ECG) signals for use in determining cardiac output. Various parameters related to the ECG signal may be used in the algorithms described hereinbelow.

As will be described hereinbelow, numerous algorithms may be applied to determine ventricular stroke volume (SV) based on impedance measurements. SV may be continuously computed and updated on a display (not shown) associated with computer 114, and may consist of a running average of the current and a user-selectable number of preceding cardiac cycles. Cardiac output may then be computed as the product of the instantaneous average SV and the heart rate, and also displayed numerically.

The three-dimensional impedance field is determined by combining the measurements from the three orthogonal pairs of sense electrodes. Hereinafter, the impedance signal will be referred to as Z, with $Z_x$, $Z_y$, and $Z_z$ being the impedance signals along each of the three orthogonal axes. $Z_0$ will be used to refer to the steady state impedance, with $Z_{0x}$, $Z_{0y}$, and $Z_{0z}$ being the steady state impedance along each of the three orthogonal axes. A signal corresponding to the difference between the impedance and the mean of the impedance signal over time will be referred to hereinafter as DZ, while signals representing this difference along each of the three axes will be referred to hereinafter as $DZ_x$, $DZ_y$, and $DZ_z$, respectively. These signals are combined according to one of the algorithms detailed hereinbelow to provide a metric for cardiac output. The three-dimensional impedance field ($DZ_{3D}$) may be calculated from these measurements as:

$$DZ_{3D} = \sqrt{DZ_x^2 + DZ_y^2 + DZ_z^2} \qquad (3)$$

While there are numerous previously known methods for computing cardiac output from a measurement of impedance, and many different parameters that assist in correlating impedance and stroke volume (SV), many of these equations do not properly account for positional artifacts.

For example, SV may be calculated according to the Kubicek equation, equation (4), as:

$$SV_K = \rho (L/Z_0)^2 * DZ_{Max}(RVET) \qquad (4)$$

where:

$SV_k$=ventricular stroke volume as computed by the Kubicek algorithm, ml;

$\rho$=resistivity of blood (in normal patients, about 150–200 ohm-cm/s, and can be corrected for each patient as a function of hematocrit);

L=distance between the sense electrodes, typically known as a manufacturing parameter, cm;

$Z_0$=steady state impedance between the sense electrodes, ohms;

$DZ_{Max}$=the maximum magnitude of the change of impedance (DZ); and

RVET=right ventricular ejection time.

As given in equation (4), the Kubicek equation is applied to a single pair of sense electrodes, that measure only a single impedance signal. As a result, the calculated stroke volume given by the Kubicek equation is highly position and orientation dependent.

The Bernstein-Sramek formula relating SV to impedance has a basic form similar to the form of the Kubicek equation. The Bernstein-Sramek formula may be expressed as:

$$SV_{BS} = \frac{V_{EPT}}{Z_O} \times \frac{dZ}{dt} MAX \times (VET) \qquad (5)$$

where:

$SV_{BS}$=Ventricular stroke volume, calculated by the Bernstein-Sramek formula, ml.

$V_{EPT}$=volume of the electrically participating tissue, which varies according to height, weight, and gender of the patient. $V_{EPT}$ may be calculated as:

$$V_{EPT} = \delta * (0.17H)^3 / 4.25$$

where H is the height of the patient (in cm), and $\delta$ is a scaling factor, relating height, weight, ideal weight, and relative blood volume index. It should be noted that this formulation of the Bernstein-Sramek formula assumes p, the blood resistivity to be a constant.

$Z_0$=steady state impedance between the sense electrodes, ohms.

$\frac{dz}{dt}$MAX = the maximum magnitude of the change of impedance with time.

VET=ventricular ejection time.

As with the Kubicek algorithm described above, the formulation of the Bernstein-Sramek algorithm given in equation (5) is expressed in terms of a single impedance value. The results of the Bernstein-Sramek algorithm also are highly dependent on the position and orientation of the sense electrodes.

To overcome these drawbacks of previously-known formulas, a new formulation of the Kubicek formula (equation (4)) was derived, which uses a Simpsons' integral from the start of ejection to the end of ejection. This new formulation may be expressed as:

$$SV = m \times \int_{BET}^{EET} DZ dt$$

where:
SV=Ventricular stroke volume, calculated using equation (6).
m=An empirically derived parameter giving the slope of the relationship between the stroke volume calculated in ohms*sec and true stroke volume in ml. The units of m are (ml)/(ohms*sec). The effects of inter-electrode distances, as well as other calibration data are lumped into the parameter m.
DZ=The change in impedance from the mean.
BET=The beginning of ejection time.
EET=The end of ejection time.

To reduce this dependency of the parameter m in equation (6) on the orientation and positioning of the sense electrodes, a three-dimensional version of the algorithm has been formulated as:

$$SV_{S3D} = \left[ \left( m_x \times \int_{BET}^{EET} DZ_x dt \right)^2 + \left( m_y \times \int_{BET}^{EET} DZ_y dt \right)^2 + \left( m_z \times \int_{BET}^{EET} DZ_z dt \right)^2 \right]^{\frac{1}{2}}$$ (7)

where:
$SV_{S3D}$=Ventricular stroke volume, computed using equation (7).
$m_x$, $m_y$, and $m_z$=Empirically determined scaling factors along each of three orthogonal axes.
$DZ_x$, $DZ_y$, and $DZ_z$=The change in impedance from the mean along each of three orthogonal axes, as measured by the apparatus of the present invention.
BET=The beginning of ejection time.
EET=The end of ejection time.

The empirically determined scaling factors $m_x$, $m_y$, and $m_z$, recognize the fact that no simple physical model can adequately relate the impedance signal and cardiac output.

Each of the three individual x, y, and z terms in the three-dimensional formulation of the equation (7) may be used separately as an indicator of stroke volume, but equation (7) normalizes the effect of sense electrode position and orientation.

In accordance with the principles of the present invention, a three-dimensional equation based on the maximum of the first derivative of the change in impedance also may be derived:

$$SV_{Diff-3D} = \left[ \left( m_{xD} \frac{dDZ_x}{dt} MAX \right)^2 + \left( m_{yD} \frac{dDZ_y}{dt} MAX \right)^2 + \left( m_{zD} \frac{dDZ_z}{dt} MAX \right)^2 \right]^{\frac{1}{2}}$$ (8)

where:
$SV_{Diff-3D}$=Ventricular stroke volume, computed using equation (8).
$m_{xD}$, $m_{yD}$, and $m_{zD}$=Empirically derived scaling factors related to the change in flow over time.
$DZ_x$, $DZ_y$, and $DZ_z$=change in impedance from the mean along each of three orthogonal axes.

Equation (8) provides a differential term, that represents three-dimensional changes in flow velocity with time. As before, the three empirically derived m parameters recognize the lack of a simple physical model relating impedance with cardiac output. Once again, each of the three individual terms for each of the axes may be useful in computing the ventricular stroke volume.

Other parameters also may be useful for computing stroke volume from an impedance signal. For example, it is possible to determine whether there is turbulence in the flow from the timing of the impedance signal. This information is useful, since the presence of turbulence indicates a high flow rate, with velocities exceeding the Reynolds number. Conversely, the absence of turbulence indicates a lower flow rate.

When turbulence is present, the duration of high points in the impedance signal is longer, and the signal takes longer to decay. These characteristics can be measured using two turbulence-related parameters. The first of these, $\tau_{85}$, represents the time spent at 85% or more of peak flow. The time spent at 85% or more of peak amplitude is longer in beats with turbulent flows. The second parameter, $\tau_d$ represents the decay time, and measures the time between 95% of the peak amplitude of the signal on the up-slope, and 60% of the peak amplitude on the downslope.

In addition to the above-listed formulas and parameters, many other parameters may be of use in correlating impedance with cardiac output. For example, the signals $I_1$, $I_2$, $I_3$, $I_4$, and $I_5$, which represent the potential between each of the five sense electrodes 18a–18e and ground, may be useful. Other potentially useful parameters include ejection time, time to peak of the first derivative of the DZ signal, and other timing parameters derived from the impedance signal. Signals relating to an ECG, such as the timing of the R wave (i.e., the maximum peak of the ECG signal) may also be used.

A measurement of arterial pressure may also be used to improve the accuracy of the multiparameter model of the present invention. If arterial pressure is included as a parameter in the multiparameter model described hereinbelow, correlations may be improved, and error may be reduced.

Animal studies using pigs have shown that there are correlations between the impedance signal (Z), the change in impedance from the mean (DZ), the integral of the signal $$\left(\int_{BET}^{EET} DZ dt\right),$$

and the maximum differential $$\left(\frac{dDZ}{dt} \text{MAX}\right)$$

of the signal and the true cardiac output. Three-dimensional forms of these signals, provided by the apparatus and methods of the present invention, have a degree of invariance to position and orientation of the sense electrodes that are used to take the measurements. Additional parameters, such as the turbulence parameters $\tau_{85}$ and $\tau_d$, as well as the other parameters discussed above are also useful.

Initial animal studies have shown that none of the foregoing individual correlations are sufficiently robust to provide an invariant relationship between impedance and true cardiac output across individual animals, without calibration, when used with the three-dimensional impedance measurement device of the present invention. In accordance with the principles of the present invention, it is therefore desirable to use optimization techniques, such as linear regression, adaptive filtering, or neural networks to generate an algorithm that uses a combination of the equations and parameters described above to correlate impedance as measured along three orthogonal axes with cardiac output.

In accordance with the principles of the present invention, an algorithm may be generated using stepwise multiple linear regression with all of the equations and parameters that individually correlate with stroke volume. The algorithm generated by this technique has the form:

$$SV = C + \Sigma W_i \times f_i \quad (9)$$

where:
SV=ventricular stroke volume;
C=a constant value determined by the linear regression;
$W_i$=weights assigned to the equations and/or parameters by the linear regression; and
$f_i$=selected ones of the equations and/or parameters for correlating impedance with ventricular stroke volume, as discussed hereinabove.

Figure 4:
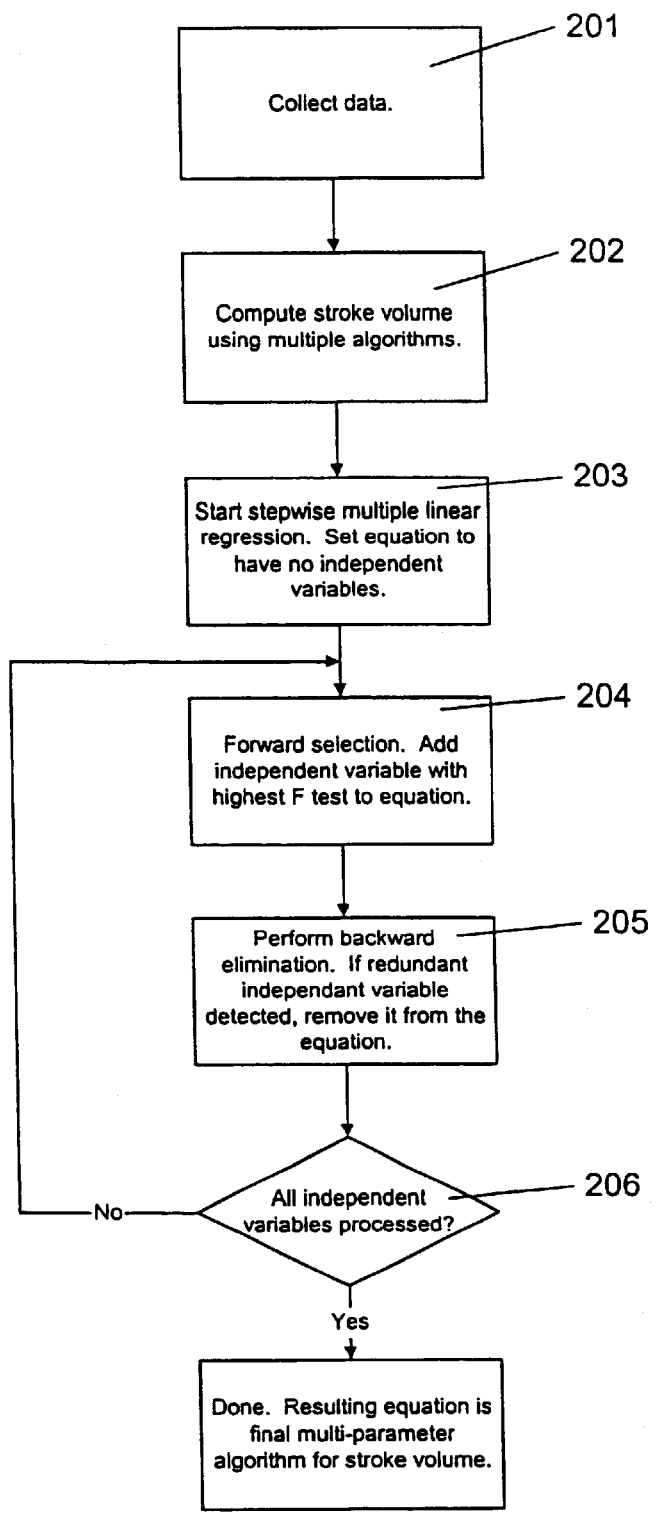
FIG. 4 is a flowchart of a method used in accordance with the principles of the present invention to derive a multi-parameter algorithm relating impedance measurements to ventricular stroke volume.

Referring to FIG. 4, a flowchart of the method of selecting independent variables for the stepwise multiple linear regression process used to derive an algorithm is discussed. At step 201, data are collected for multiple subjects under a variety of occlusion conditions. The data include impedance measurements along each of three axes, as discussed hereinabove, the $I_1$–$I_5$ measurements, and other parameters for the algorithms described hereinabove. Additionally, data are collected on the actual stroke volume, using, for example, a transit time flow probe.

At step 202, the data are used with the various algorithms to compute a predicted stroke volume for each of the algorithms. These results, as well as the measurements of impedance, $I_1$–$I_5$, and other parameters that correlate with stroke volume are used as independent variables in the stepwise multiple linear regression.

At step 203, the stepwise multiple linear regression equation begins with no independent variables. At step 204, the independent variable with the highest F test is added to the equation, in a manner similar to forward selection.

At step 205, backwards elimination is performed on the set of independent variables to test for redundancy. If a redundant variable is detected, it is eliminated.

Finally, at step 206, the forward selection (step 204) and backward elimination (step 205) are repeated until all of the independent variables have been added to the equation, or have been eliminated from the equation.

This technique combines the best characteristics of forward selection and backward elimination. The first variable added is the strongest predictor of the dependent variable and redundant independent variables are eliminated. This method is used to determine which parameters will be included in the final multi-parameter algorithm for stroke volume.

Once the final multi-parameter algorithm for stroke volume is determined, it may be used with the apparatus of the present invention to monitor cardiac output by programming computer 114 to continuously apply the final multi-parameter algorithm to compute the stroke volume from the data collected by the sense electrodes. Cardiac output may then be computed as the product of the instantaneous average stroke volume and the heart rate.

Other optimization techniques also may be used to derive a multi-parameter algorithm for stroke volume. Some of the techniques which were tried as alternatives to stepwise multiple linear regression included use of a multilayer perceptron neural network, and an algorithm that used fuzzy logic to determine signal quality, and to select a multi-parameter algorithm derived through multiple linear regression according to the available high quality signals. These techniques provided results that were similar to the results obtained using the multi-parameter algorithm derived using the stepwise multiple linear regression method described hereinabove.

Figure 5:
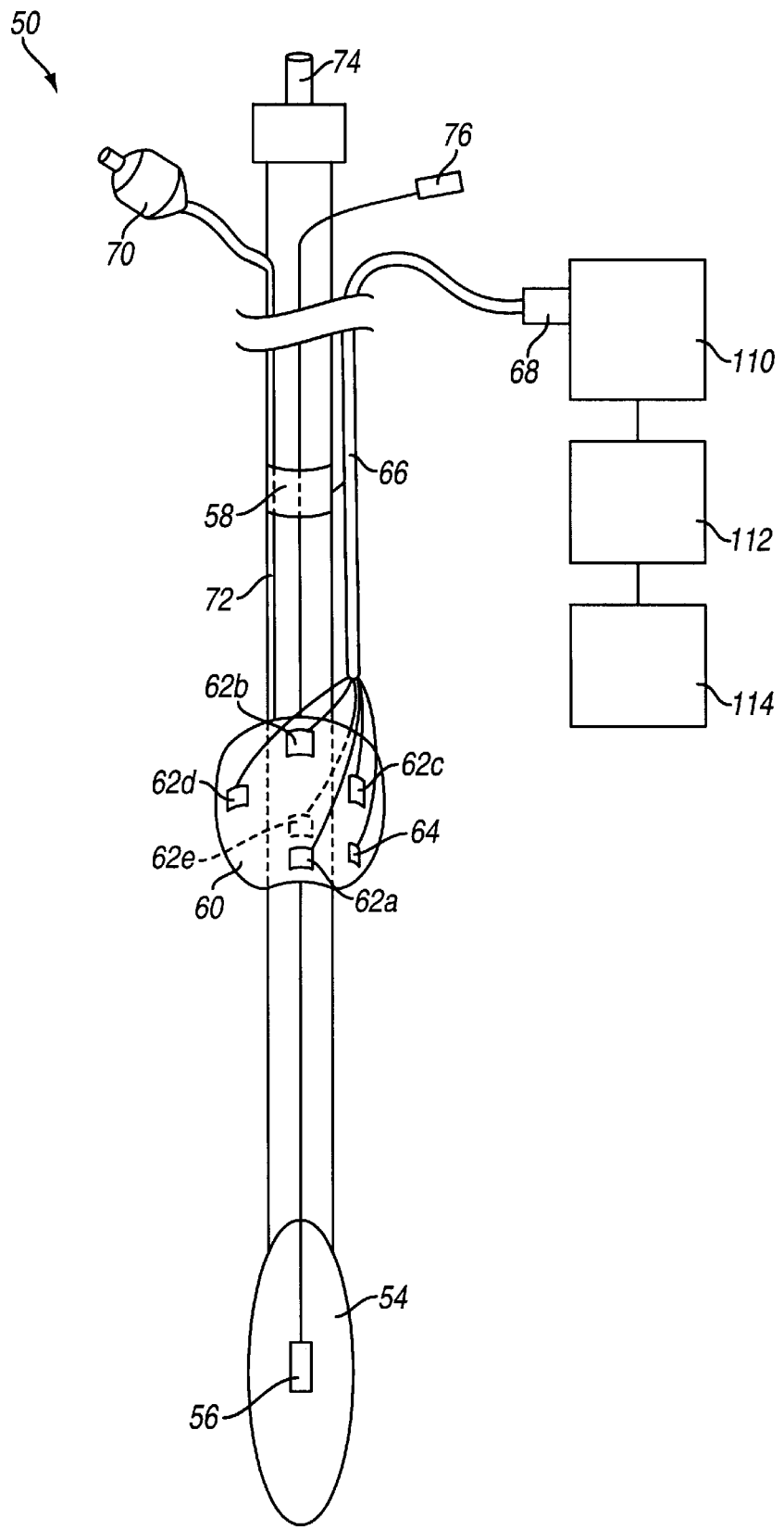
FIG. 5 shows a second embodiment of the apparatus of the present invention for esophageal use.

Referring now to FIG. 5, an alternative embodiment of the three-dimensional impedance measurement device of the present invention is described, which is designed for esophageal use, rather than tracheal use. This embodiment may be advantageously used, for example, in previously intubated patients. Extubating a patient having an endotracheal tube to replace it with a tube having sensors for measuring impedance in accordance with the principles of the present invention may involve an unacceptable degree of discomfort or risk to the patient. By using the embodiment shown in FIG. 5, however, in which a set of electrodes is added to an esophageal stethoscope, impedance measurements may be used to compute cardiac output in previously intubated patients without disturbing an endotracheal tube that is already in place.

Measurement apparatus 50 comprises an esophageal stethoscope, including tube 53, stethoscope balloon 54 disposed at a distal end of tube 53, and thermister 56. Shaft electrode 58, which serves as an electrical ground electrode for measurement apparatus 50, is mounted on tube 53. Inflatable cuff 60 also is mounted on tube 53, and sense electrodes 62a–62e are mounted on inflatable cuff 60 to form three orthogonal pairs of sense electrodes. Additionally, current electrode 64 is mounted on inflatable cuff 60.

All of the electrodes, including shaft electrode 58, sense electrodes 62a–62e, and current electrode 64 are connected via cable 66 and connector 68 to impedance recorder 110. Cable 66 may comprise a shielded cable containing multiple conductors or a ribbon cable, and may be disposed within tube 53, parallel to tube 53, or wrapped around tube 53. Measurement apparatus 50 also includes digital sampler 112, and computer 114.

As in the embodiment of FIG. 3, sense electrodes 62a–62e, current electrode 64, and shaft electrode 58 preferably are composed of a conductive silver ink, printed or silk screened onto a polyethylene backing. Sense electrodes 62a–62e and current electrode 64 preferably are each 6 mm square, while shaft electrode 58 preferably comprises a 15 mm wide band. It will be understood by one skilled in the relevant arts that other dimensions may be used, and that the size of inflatable cuff 60 and the sizes and spacing of the electrodes may be larger in the esophageal embodiment than in the endotracheal embodiment described hereinabove, due to the larger diameter of the esophagus.

The interior of inflatable cuff 60 is in fluid communication with insufflation port 70 via lumen 72. When inflated, inflatable cuff 60 retains the esophageal stethoscope in position within the patient's esophagus, thereby preventing inadvertent movement. Inflatable cuff 60 also urges sense electrodes 62a–62e and current electrode 64 into contact with the interior wall of the esophagus. Inflatable cuff 60 may be inflated using conventional inflation means (i.e., a gas filled syringe) connected to insufflation port 70 via lumen 72. Alternatively, inflatable cuff 60 may be replaced by another suitable type of expandable member for urging the electrodes against the interior wall of the patient's esophagus, such as an expanding mandrel, or other mechanical arrangement.

In addition to measuring impedance signals through electrodes, the esophageal stethoscope of measurement apparatus 50 may be used for ascultation and temperature measurements. To accommodate use of these functions, measurement apparatus 50 includes stethoscope hookup 74, and thermister lead 76. Preferably, stethoscope hookup 74 and thermister lead 76 may be connected to standard recording equipment.

In use, tube 53 is inserted through the mouth into a patient's esophagus, and positioned so that inflatable cuff 60 is located near the aorta. Inflatable cuff 60 is then inflated, causing sense electrodes 62a–62e and current electrode 64 to contact the interior wall of the patient's esophagus. Shaft electrode 58 contacts the esophagus several centimeters above the aorta, and serves as a ground electrode.

An alternating current, preferably a sinusoidal current having a predetermined frequency, is applied between current electrode 64 and shaft electrode 58 by impedance recorder 110. The alternating current preferably has an amplitude of approximately 2 mA, and a frequency in the range of 5 KHz to 1 MHz, typically 100 KHz.

As for the endotracheal embodiment discussed hereinabove, signals indicative of a drop in voltage between the two electrodes of each of the orthogonal pairs of electrodes are received at impedance recorder 110. The first orthogonal pair of electrodes comprises sense electrodes 62a and 62b, the second orthogonal pair of electrodes comprises sense electrodes 62c and 62d, and the third orthogonal pair comprises sense electrodes 62a and 62e.

These impedance signals are digitally sampled at fixed intervals, preferably approximately 400 samples per second, by digital sampler 112. The digital samples are provided to computer 114, which may record the samples, display graphs of the samples, apply algorithms in accordance with the principles of the present invention to determine cardiac output, or apply any other algorithms to the digital samples.

A multi-parameter algorithm similar to that discussed hereinabove computes the stroke volume based on impedance measurements. The algorithm may be derived using stepwise multiple linear regression, in the manner described hereinabove.

Further alternative embodiments of the present invention also may include additional sensors to enable other types of quantitative analysis. For example, diodes suitable for employing blood oximetry techniques based on near infrared light absorption also may be disposed on the endotracheal tube to measure blood oxygen saturation levels. In particular, multiple light emitting diodes, including one or more red-light and infrared emitting diodes, may be disposed on the endotracheal tube, on the inflatable cuff or member, or both, for obtaining blood oxygen saturation measurements using transreflectance oximetry techniques, as described, for example, in U.S. Pat. No. 5,099,842, the entirety of which is incorporated herein by reference.

Figure 6A:
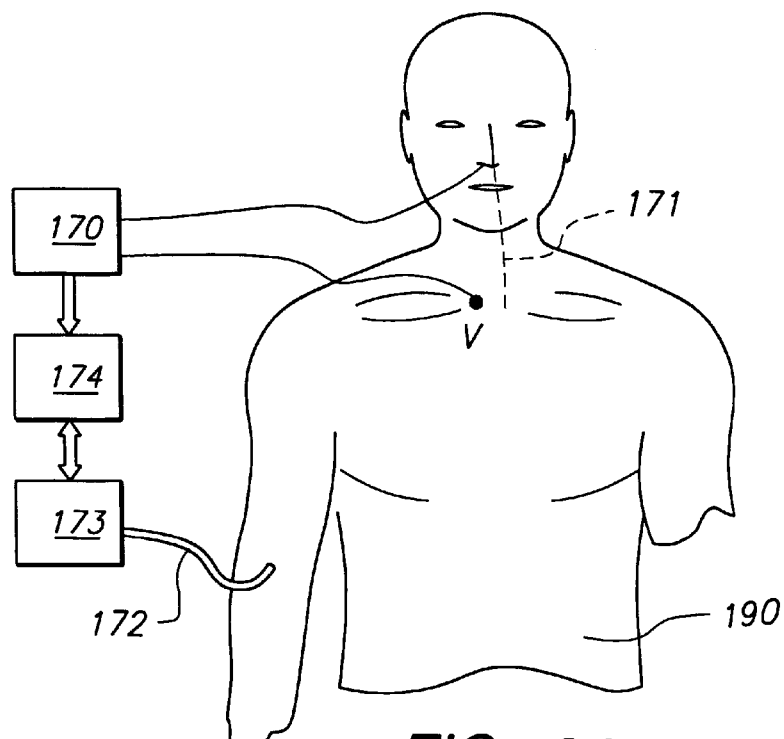
FIGS. 6A and 6B are, respectively, schematic diagrams showing systems for administering fluids or medication to a patient and for controlling heart rate for patients having pacemakers, respectively, constructed in accordance with the principles of the present invention.

Referring now to FIG. 6A, use of the apparatus of the present invention is described as a controller for the administration of fluids, or of medication, such as dobutamine, dopamine, epinephrine, norepinephrine, nitroprusside, or other substances for medical management of hemodynamics. In FIG. 6A, cardiac output is measured by apparatus 170, which may be either of the foregoing embodiments, and includes tube 171 disposed in patient 190, either in the trachea or the esophagus. Apparatus 170 is used to monitor hemodynamic status and as a metric to control the administration of fluids or medication intravenously via lumen 172 coupled to fluid supply system 173. Computer 174, which may be the same computer that computes cardiac output from the impedance values output by impedance recorder 110 and digital sampler 112, controls fluid supply system 172. The apparatus of FIG. 6A provides a closed-loop system wherein the amount of fluid or other medication injected into the patient is controlled by the cardiac output computed as described hereinabove.

Figure 6B:
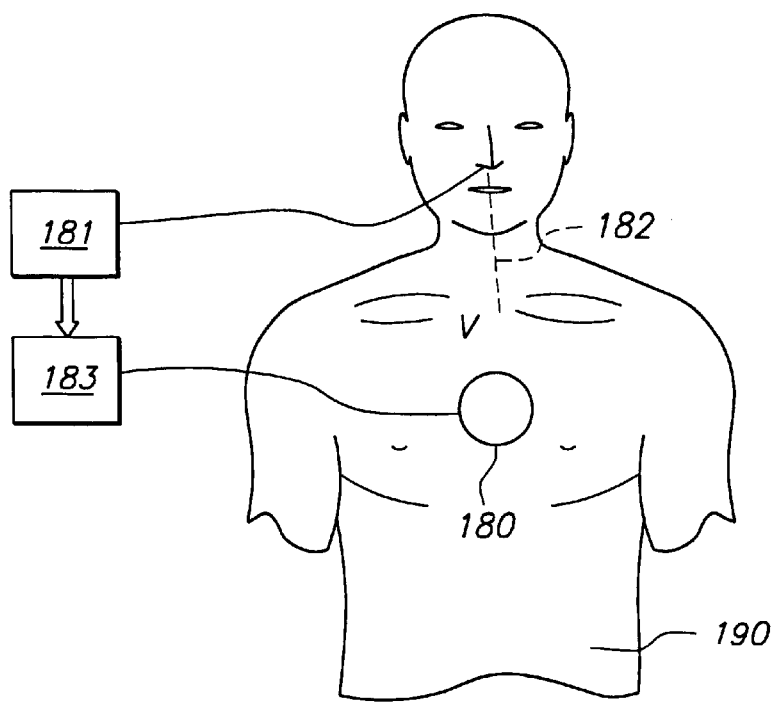

Referring now to FIG. 6B, use of the apparatus of the present is described as a controller for pacemaker 180. Generally, it is desirable to maximize cardiac output for the lowest possible heart rate, since the lower the heart rate, the lower the myocardial oxygen consumption. In the arrangement of FIG. 6B, cardiac output is measured by apparatus 181, which may be any of the foregoing embodiments, and includes tube 182 disposed in patient 190, either in the trachea or the esophagus. The output of apparatus 181 is used, in conjunction with computer 183, as a metric to control the setting of pacemaker 180 as described hereinafter.

A baseline cardiac output measurement is first obtained and then the heart rate is reduced by a predetermined amount, e.g., two beats/min, while the cardiac output is continuously monitored by apparatus 181. As long as the cardiac output increases or remains unchanged, the heart rate is periodically further lowered by the predetermined amount, for example, by 2 beats/min every 15 minutes. The process of reducing heart rate while monitoring cardiac output is continued until either a minimum desired heart rate is obtained or the cardiac output measured by apparatus 181 begins to decrease. If the cardiac output is determined to have decreased, the heart rate is returned to the preceding higher rate.

EXAMPLE

When the above described stepwise multiple linear regression technique was applied to data taken from ten pigs, using the apparatus of the present invention, the resulting multi-parameter algorithm contained weighted terms for 53 parameters, including $I_1, I_2, I_3, I_4, I_5, Z_{0x}, Z_{0y}, Z_{0z}$, equation (7), each of the x, y, and z terms of equation (7), equation (8), and each of the x, y, and z terms of the equation (8), and other parameters relating to timing, and to the ECG signal. The resulting algorithm was able to compute a stroke volume from the various impedance measurements while maintaining a high degree of invariance to exact positioning and rotation of the sense electrodes, and an ability to be used across individuals without need for recalibration for each individual in which the device was used. Table 1 shows the list of independent variables (i.e., parameters) in the equation that resulted from stepwise linear regression, and the weight assigned to each of the parameters. In accordance with equation (9), described hereinabove, to compute stroke volume, the weight of each parameter is multiplied by the value of the parameter, and the results for all weights and parameters are summed. A constant value is then added to the sum to provide the metric for stroke volume. For the equation with weights and parameters shown in Table 1, the constant, C=55.935091.

TABLE 1

Weights and Parameters for Example Algorithm

| | Weight | Parameter | Description |
|---|---|---|---|
| 1 | −3.407786 | $Z_{0x}$ | |
| 2 | −2.167552 | $Z_{0y}$ | |
| 3 | −1.178316 | $Z_{0z}$ | |
| 4 | −3.452352 | $I_1$ | |
| 5 | 2.116957 | $I_2$ | |
| 6 | 1.038714 | $I_3$ | |
| 7 | −1.217662 | $I_4$ | |
| 8 | 0.267879 | $I_5$ | |
| 9 | −488.79698 | $SV_{S3D}$ | Equation (7) |
| 10 | 2.734155 | $SV_{Diff-3D}$ | Equation (8) |
| 11 | 0.560702 | $SV_{Diff-3D}$ | Equation (8) using maximum of the first derivative of DZ within 100 milliseconds of the R wave. |
| | | (near R wave) | |
| 12 | −0.082627 | $INFLEC_x$ | Milliseconds between the max and the min of the first derivative of $DZ_x$. |
| 13 | −733.61 | $CONCA_x$ | Area in ohms/sec bounded by the $DZ_x$ trace and the line passing through the 0.95*max $DZ_x$ rise point and the 0.40*max $DZ_x$ decay point. |
| 14 | −0.069485 | $BIN1DZ_x$ | Number of samples in the band of 20% of the max $DZ_x$ trace. |
| 15 | −0.004758 | $DECAY_x$ | Milliseconds between the 0.85*max $DZ_x$ rise point and the 0.40*max $DZ_x$ decay point (similar to $T_d$). |
| 16 | 739.2874 | $Z_xVOL$ | Integral of the $DZ_x$ trace (i.e. the x term of equation (7)). |
| 17 | −13.339431 | $MXDZDT_x$ | Max of the first derivative of $DZ_x$ (i.e. the x term of equation (8)). |
| 18 | −0.084653 | $MXDZDT_xS$ | Milliseconds between the R wave and the max of the first derivative of $DZ_x$. |
| 19 | 6.292195 | $MXDZDTW_x$ | Max of the first derivative of $DZ_x$ within 100 milliseconds of the R wave. |
| 20 | −0.036876 | $MXDZDTW_xS$ | Milliseconds between the R wave and the max of the first derivative of $DZ_x$, within 100 milliseconds of the R wave. |
| 21 | 7.879514 | $MNDZDT_x$ | Min of the first derivative of $DZ_x$. |
| 22 | 0.078928 | $MNDZDT_xE$ | Milliseconds between the R wave and the min of the first derivative of $DZ_x$. |
| 23 | −3.040184 | $MNDZDTW_x$ | Min of the first derivative of $DZ_x$ within 350 milliseconds of the R wave. |

TABLE 1-continued

Weights and Parameters for Example Algorithm

| | Weight | Parameter | Description |
|---|---|---|---|
| 24 | −0.038439 | $MNDZDTW_xE$ | Milliseconds between the R wave and the min of the first derivative of $DZ_x$, within 350 milliseconds of the R wave. |
| 25 | 103.84647 | $MAXDZ_x$ | Max of the $DZ_x$ trace. |
| 26 | −0.32096 | $INFLEC_y$ | See $INFLEC_x$, but for $DZ_y$. |
| 27 | 1333.1547 | $CONCA_y$ | See $CONCA_x$, but for $DZ_y$. |
| 28 | 0.297539 | $BIN2DZ_y$ | Number of samples in the band bounded by 20% and 40% of max $DZ_y$. |
| 29 | 0.067632 | $DECAY_y$ | See $DECAY_x$, but for $DZ_y$. |
| 30 | 578.72077 | $Z_yVOL$ | See $Z_xVOL$, but for $DZ_y$. |
| 31 | −6.133654 | $MXDZDT_y$ | See $MXDZDT_x$, but for $DZ_y$. |
| 32 | −0.324225 | $MXDZDT_yS$ | See $MXDZDT_xS$, but for $DZ_y$. |
| 33 | 10.405067 | $MXDZDTW_y$ | See $MXDZDTW_x$, but for $DZ_y$. |
| 34 | −0.223327 | $MXDZDTW_yS$ | See $MXDZDTW_xS$, but for $DZ_y$. |
| 35 | 22.520111 | $MNDZDT_y$ | See $MNDZDT_x$, but for $DZ_y$. |
| 36 | 0.293328 | $MNDZDT_yE$ | See $MNDZDT_xE$, but for $DZ_y$. |
| 37 | −10.853298 | $MNDZDTW_y$ | See $MNDZDTW_x$, but for $DZ_y$. |
| 38 | 0.060624 | $MNDZDTW_yE$ | See $MNDZDTW_xE$, but for $DZ_y$. |
| 39 | 13.229832 | $MXDZ_y$ | Max of the $DZ_y$ trace. |
| 40 | −0.219214 | $INFLEC_z$ | See $INFLEC_x$, but for $DZ_z$. |
| 41 | 2.146938 | $CONCA_z$ | See $CONCA_x$, but for $DZ_z$. |
| 42 | 0.266825 | $BIN2DZ_z$ | See $BIN2DZ_x$, but for $DZ_z$. |
| 43 | 0.045675 | $DECAY_z$ | See $DECAY_x$, but for $DZ_z$. |
| 44 | 746.7884 | $Z_zVOL$ | See $Z_xVOL$, but for $DZ_z$. |
| 45 | 4.463351 | $MXDZDT_z$ | See $MXDZDT_x$, but for $DZ_z$. |
| 46 | −0.21119 | $MXDZDT_zS$ | See $MXDZDT_xS$, but for $DZ_z$. |
| 47 | 23.561712 | $MXDZDTW_z$ | See $MXDZDTW_x$, but for $DZ_z$. |
| 48 | −0.126598 | $MXDZDTW_zS$ | See $MXDZDTW_xS$, but for $DZ_z$. |
| 49 | −2.202599 | $MNDZDT_z$ | See $MNDZDT_x$, but for $DZ_z$. |
| 50 | 0.206271 | $MNDZDT_zE$ | See $MNDZDT_xE$, but for $DZ_z$. |
| 51 | 0.325518 | $MNDZDTW_z$ | See $MNDZDTW_x$, but for $DZ_z$. |
| 52 | 0.007671 | $MNDZDTW_zE$ | See $MNDZDTW_zE$, but for $DZ_z$. |
| 53 | −203.33016 | $MXDZ_z$ | Max of the $DZ_z$ trace. |

Figure 7:
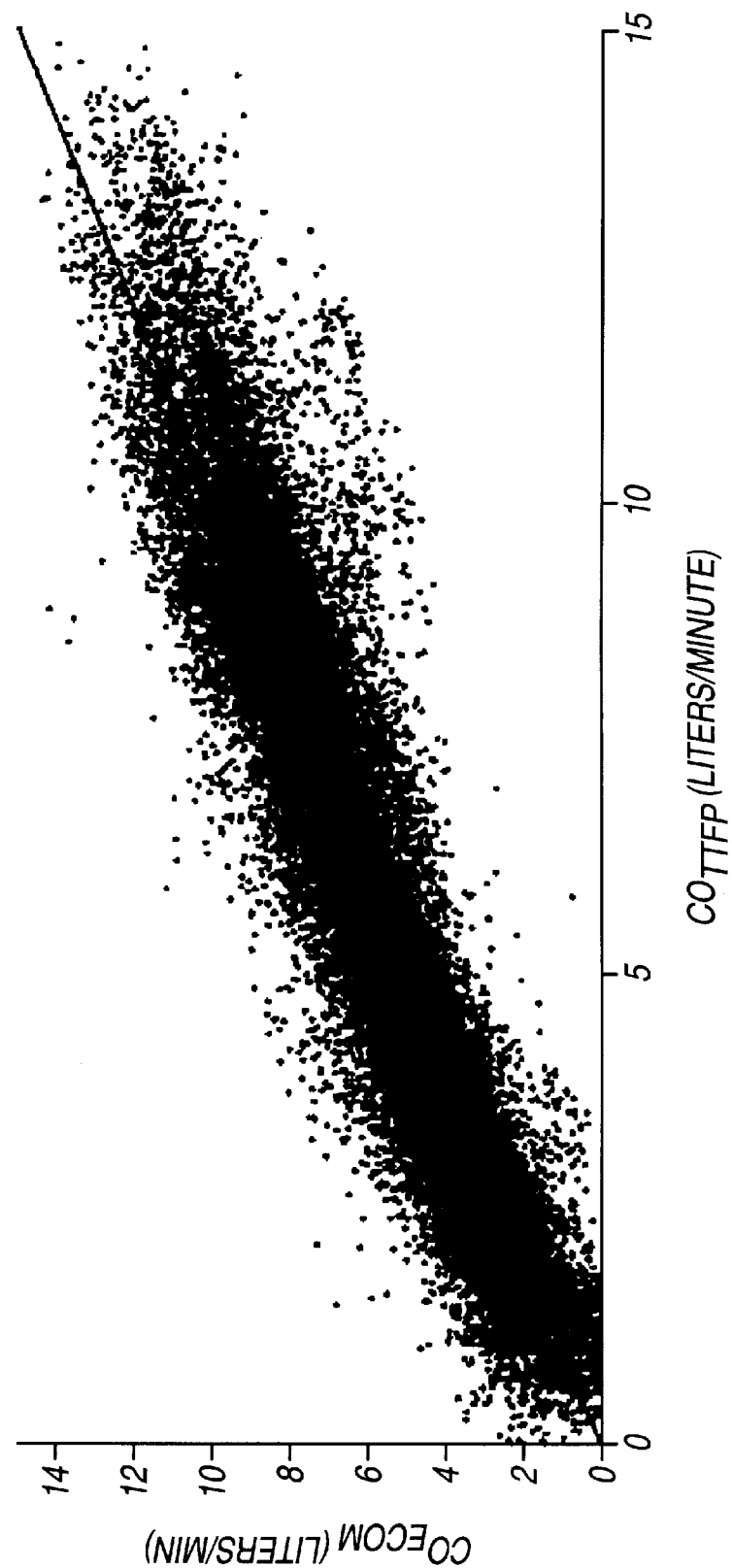
FIG. 7 is a graph showing results obtained using apparatus and methods in accordance with the present invention in animals.

FIG. 7 shows the results of a test of the apparatus and derived algorithm of Table 1 on a group of ten pigs. The axis labeled $CO_{ECOM}$ shows the cardiac output calculated from impedance measurements taken with the apparatus of the present invention by the multi-parameter algorithm with the weights and parameters given in Table 1. The axis labeled $CO_{TTFP}$ shows the cardiac output determined by a transit time flow probe. The data shown in the graph is from 29,657 heart beats recorded during occlusion tests from the ten animals during a 24 hour recording period.

As can be seen, there is a high degree of correlation between the cardiac output as determined by the algorithm, and the cardiac output as measured by a transit time flow probe. Since the cardiovascular system of pigs is commonly used as a model of the human cardiovascular system, it is expected that an algorithm having similar or identical independent variables, and similar weights may be derived using stepwise multiple linear regression.

Although preferred illustrative embodiments of the invention are described above, it will be obvious to one skilled in the art that various changes and modifications may be made therein without departing from the invention and that the appended claims are intended to cover all such changes and modifications which fall within the true spirit and scope of the invention. For example, the shaft electrode and/or the current electrode could be placed on a separate inflatable cuff. Additionally, applicant expects that the apparatus and methods of the present invention may be advantageously applied to animal subjects employed in clinical studies, as well as humans.

What is claimed is:

1. Apparatus for computing a metric corresponding to a patient's cardiac output, the apparatus comprising:
   a bioelectrical impedance recorder;
   a tube having a proximal portion, and a distal portion;
   an expandable member disposed on the distal portion;
   three orthogonal pairs of sense electrodes disposed on the expandable member and electrically coupled to the bioelectrical impedance recorder;
   a current electrode for injecting a current into the patient's thorax; and
   a ground electrode;
   wherein the three orthogonal pairs of sense electrodes generate signals corresponding to the bioelectrical impedance of blood flow through the aorta and the signals are provided to the bioelectrical impedance recorder.

2. The apparatus as defined in claim 1 wherein the current electrode is disposed on the expandable member.

3. The apparatus as defined in claim 1 wherein the ground electrode is disposed on the tube.

4. The apparatus as defined in claim 1 wherein the expandable member comprises an inflatable cuff, and the apparatus further comprises a lumen for inflating the inflatable cuff.

5. The apparatus as defined in claim 1 wherein at least one sense electrode belongs to at least two of the three orthogonal pairs of sense electrodes.

6. The apparatus as defined in claim 5 wherein the three orthogonal pairs of sense electrodes comprise five sense electrodes.

7. The apparatus as defined in claim 1 wherein the tube is an endotracheal tube, and wherein the expandable member is adapted to urge the three orthogonal pairs of sense electrodes into contact with the patient's tracheal mucosa.

8. The apparatus as defined in claim 7 wherein the tube is adapted to be inserted in the trachea of the patient through the mouth, a nasal passageway, or a tracheotomy port.

9. The apparatus as defined in claim 1 wherein the tube is an esophageal tube, and wherein the expandable member is adapted to urge the three orthogonal pairs of sense electrodes into contact with an interior of the patient's esophagus.

10. The apparatus as defined in claim 9 further comprising a stethoscope balloon disposed on the distal portion, the stethoscope balloon permitting the apparatus to be used as an esophageal stethoscope.

11. The apparatus as defined in claim 10 further comprising a thermister disposed in the distal portion, the thermister providing a signal indicative of temperature within the esophagus.

12. The apparatus as defined in claim 1 wherein the apparatus further comprises reference marks on the proximal end of the tube to determine circumferential orientation of the tube.

13. The apparatus as defined in claim 1 wherein the current electrode is electrically coupled to the impedance recorder, and wherein the impedance recorder injects an alternating current having a predetermined frequency through the current electrode.

14. The apparatus as defined in claim 1 further comprising a computer coupled to the impedance recorder, the computer receiving a digitized signal generated from the signals corresponding to the bioelectrical impedance of blood flow through the aorta.

15. The apparatus as defined in claim 14 wherein the computer is programmed to use a multi-parameter algorithm to calculate a metric for ventricular stroke volume from the digitized signal.

16. The apparatus as defined in claim 15 wherein the computer is further programmed to calculate the metric corresponding to the patient's cardiac output from the metric for ventricular stroke volume.

17. The apparatus as defined in claim 1 further comprising a fluid administration system for injecting a fluid into the vascular system of the patient, wherein the fluid administration system is responsive to the metric corresponding to the cardiac output.

18. The apparatus as defined in claim 1 further comprising a drug administration system for injecting a medication into the vascular system of the patient, wherein the drug administration system is responsive to the metric corresponding to the cardiac output.

19. The apparatus as defined in claim 18 wherein the medication comprises one or more of dobutamine, dopamine, epinephrine, norepinephrine, and nitroprusside.

20. The apparatus as defined in claim 1 further comprising a pacemaker controlling the heart rate of the patient, wherein the pacemaker is responsive to the metric corresponding to the cardiac output.

21. A method of measuring the cardiac output of an organism comprising steps of:
   positioning three orthogonal pairs of sense electrodes within the organism in the vicinity of the aorta;
   injecting a current into the thorax of the organism through a current electrode;
   applying a voltage between the current electrode and a ground electrode so that a current flows through the tissues of the organism disposed between the current electrode and the ground electrode; and
   detecting voltages developed across the three orthogonal pairs of sense electrodes caused by the current flowing in the tissues of the organism, the voltages varying in accordance with changes in the bioelectrical impedance of the tissues.

22. The method as defined in claim 21 wherein positioning three orthogonal pairs of sense electrodes comprises positioning three orthogonal pairs of sense electrodes within the organism's trachea, so that the three orthogonal pairs of sense electrodes contact the organism's tracheal mucosa in a position near the aorta.

23. The method as defined in claim 21 wherein positioning three orthogonal pairs of sense electrodes comprises positioning three orthogonal pairs of sense electrodes within the organism's esophagus, so that the three orthogonal pairs of sense electrodes contact an interior surface of the organism's esophagus at a position near the aorta.

24. The method as defined in claim 21 wherein injecting a current comprises injecting an alternating current having a predetermined frequency between the current electrode and the ground electrode.

25. The method as defined in claim 21 wherein the steps of applying a voltage between the current electrode and the ground electrode and detecting a voltage developed across the three orthogonal pairs of sense electrodes are performed continuously.

26. The method as defined in claim 21 further comprising computing a metric for ventricular stroke volume from the voltages detected by the three orthogonal pairs of sense electrodes using a multi-parameter algorithm.

27. The method as defined in claim 26 further comprising deriving the multi-parameter algorithm using a stepwise multiple linear regression technique.

28. The method as defined in claim 26 further comprising computing a metric for the cardiac output of the organism from the metric for ventricular stroke volume.

29. The method as defined in claim 21 further comprising steps of:
 providing a fluid administration system for injecting a fluid intravenously into the organism's vascular system; and
 periodically actuating the fluid administration system responsive to the detected voltage developed across the three orthogonal pairs of sense electrodes.

30. The method as defined in claim 21 further comprising steps of:
 providing a drug administration system for injecting a medication intravenously into the organism's vascular system; and
 periodically actuating the drug administration system responsive to the detected voltage developed across the three orthogonal pairs of sense electrodes.

31. The method as defined in claim 21 further comprising steps of:
 providing a pacemaker electrically coupled to the heart of the organism to control heart rate; and
 adjusting the heart rate responsive to voltage developed across the three orthogonal pairs of sense electrodes to optimize cardiac output.

32. The method as defined in claim 31 wherein the step of adjusting the heart rate comprises a step of lowering the heart rate to obtain either a predetermined minimum heart rate or until the cardiac output is measured to be decreasing.

33. Apparatus for detecting a three-dimensional bioimpedance field in the vicinity of a patient's aorta, the apparatus comprising:
 a tube having a proximal portion, and a distal portion;
 an expandable member disposed on the distal portion;
 three orthogonal pairs of sense electrodes disposed on the expandable member;
 a current electrode for injecting a current into the patient's thorax; and
 a ground electrode;
 wherein the three orthogonal pairs of sense electrodes generate signals corresponding to the bioelectrical impedance of blood flow through the aorta.

34. The apparatus as defined in claim 33 wherein the current electrode is disposed on the expandable member.

35. The apparatus as defined in claim 33 wherein the ground electrode is disposed on the tube.

36. The apparatus as defined in claim 33 wherein the expandable member comprises an inflatable cuff, and the apparatus further comprises a lumen for inflating the inflatable cuff.

37. The apparatus as defined in claim 33 wherein at least one sense electrode belongs to at least two of the three orthogonal pairs of sense electrodes.

38. The apparatus as defined in claim 37 wherein the three orthogonal pairs of sense electrodes comprise five sense electrodes.

39. The apparatus as defined in claim 33 wherein the tube is an endotracheal tube, and wherein the expandable member is adapted to urge the three orthogonal pairs of sense electrodes into contact with the patient's tracheal mucosa.

40. The apparatus as defined in claim 39 wherein the tube is adapted to be inserted in the trachea of the patient through the mouth, a nasal passageway, or a tracheotomy port.

41. The apparatus as defined in claim 33 wherein the tube is an esophageal tube, and wherein the expandable member is adapted to urge the three orthogonal pairs of sense electrodes into contact with the interior of the patient's esophagus.

42. The apparatus as defined in claim 41 further comprising a stethoscope balloon disposed on the distal portion, the stethoscope balloon permitting the apparatus to be used as an esophageal stethoscope.

43. The apparatus as defined in claim 38 further comprising a thermister disposed in the distal portion, the thermister providing a signal indicative of temperature within the esophagus.

* * * * *